United States Patent
McEwen et al.

(10) Patent No.: US 7,479,154 B2
(45) Date of Patent: Jan. 20, 2009

(54) SURGICAL TOURNIQUET APPARATUS FOR MEASURING LIMB OCCLUSION PRESSURE

(76) Inventors: James A. McEwen, c/o Western Clinical Engineering Ltd., Suite 207, 1099 West 8th Avenue, Vancouver, British Columbia (CA) V7G 1S9; Michael Jameson, c/o Western Clinical Engineering Ltd., Suite 207, 1099 West 8th Avenue, Vancouver, British Columbia (CA) V7G 1S9; Allen Upward, c/o Western Clinical Engineering Ltd., Suite 207, 1099 West 8th Avenue, Vancouver, Britsh Columbia (CA) V7G 1S9

( * ) Notice: Subject to any disclaimer, the term of this patent is extended or adjusted under 35 U.S.C. 154(b) by 435 days.

(21) Appl. No.: 11/122,600

(22) Filed: May 5, 2005

(65) Prior Publication Data

US 2006/0253150 A1    Nov. 9, 2006

(51) Int. Cl.
*A61B 17/00* (2006.01)
(52) U.S. Cl. ........................................ 606/202; 606/203
(58) Field of Classification Search ................. 606/201, 606/202, 203; 600/478, 500
See application file for complete search history.

(56) References Cited

U.S. PATENT DOCUMENTS

| | | | |
|---|---|---|---|
| 3,552,383 | A | 1/1971 | Krueger |
| 4,321,929 | A | 3/1982 | Lemelson |
| 4,469,099 | A | 9/1984 | McEwen |
| 4,479,494 | A | 10/1984 | McEwen |
| 4,520,819 | A | 6/1985 | Birmingham |

(Continued)

FOREIGN PATENT DOCUMENTS

CA    2198482 A1    3/1996

(Continued)

OTHER PUBLICATIONS

Younger et al; Wide Contoured Thigh Cuffs and Automated Limb Occlusion Measurement Allow Lower Tourniquet Pressures; Clinical Orthopaedics and Related Research; Nov. 2005; pp. 286-293; No. 428.

(Continued)

*Primary Examiner*—Todd E Manahan
*Assistant Examiner*—Eric Blatt
(74) *Attorney, Agent, or Firm*—Hancock Hughey LLP

(57) ABSTRACT

Tourniquet apparatus for rapidly and accurately measuring a patient's limb occlusion pressure comprises: an inflatable tourniquet cuff for encircling a limb at a location; a tourniquet instrument releasably connectable to the cuff that includes: pressure sensing means for producing a cuff pressure signal indicative of the level of pressure in the cuff; pressure regulation means communicating with the cuff and responsive to the cuff pressure signal for regulating the pressure in the cuff near a reference pressure level; blood flow transducing means adapted for applying to a portion of the limb distal to the cuff to produce a blood flow signal indicative of blood flow in the portion; and limb occlusion pressure means responsive to the blood flow signal and the cuff pressure signal and operable for detecting arterial pulsations of blood flow, for increasing the reference pressure level in synchrony with the arterial pulsations and for producing a limb occlusion pressure value indicative of the lowest cuff pressure at which the magnitude of the arterial pulsations is less than a minimum detection threshold.

14 Claims, 5 Drawing Sheets

U.S. PATENT DOCUMENTS

| | | | |
|---|---|---|---|
| 4,635,635 A | | 1/1987 | Robinette-Lehman |
| 4,671,290 A | | 6/1987 | Miller |
| 5,246,002 A | * | 9/1993 | Prosser ..................... 600/336 |
| 5,254,087 A | | 10/1993 | McEwen |
| 5,439,477 A | | 8/1995 | McEwen |
| 5,454,831 A | | 10/1995 | McEwen |
| 5,485,838 A | * | 1/1996 | Ukawa et al. ............... 600/330 |
| 5,556,415 A | | 9/1996 | McEwen |
| 5,584,853 A | * | 12/1996 | McEwen ..................... 606/201 |
| 5,607,447 A | | 3/1997 | McEwen |
| 5,649,954 A | | 7/1997 | McEwen |
| 5,681,339 A | | 10/1997 | McEwen |
| 5,741,295 A | | 4/1998 | McEwen |
| 5,855,589 A | | 1/1999 | McEwen |
| 5,911,735 A | * | 6/1999 | McEwen et al. ............ 606/201 |
| 5,931,853 A | | 8/1999 | McEwen |
| 5,935,146 A | | 8/1999 | McEwen |
| 5,968,073 A | | 10/1999 | Jacobs |
| 6,051,016 A | | 4/2000 | Mesaros |
| 6,299,629 B1 | * | 10/2001 | Gruenfeld et al. ........... 606/202 |
| 6,475,228 B1 | | 11/2002 | Mesaros |
| 6,589,267 B1 | | 7/2003 | Hui |
| 6,605,103 B2 | * | 8/2003 | Hovanes et al. ............. 606/202 |
| 7,074,177 B2 | * | 7/2006 | Pickett et al. ................. 600/17 |
| 2004/0147956 A1 | | 7/2004 | Hovanes |

FOREIGN PATENT DOCUMENTS

| | | |
|---|---|---|
| CA | 2198498 A1 | 3/1996 |
| CA | 2260142 A1 | 2/1998 |
| CA | 2424398 A1 | 5/2002 |
| CA | 2534329 A1 | 2/2005 |

OTHER PUBLICATIONS

Bussani et al; Improved Tacking of Limb Occlusion Pressure for Surgical Tourniquet; IEEE Transactions on Biomedical Engineering; Apr. 1988; pp. 221-229; vol. 34 No. 4.

McEwen et al; An adaptive Tourniquet for Improved Safety in Surgery; IEEE Transactions on Biomedical Engineering; Feb. 1982; pp. 122-128; vol. 29 No. 2.

CIPO, International Search Report issued in corresponding App. PCT/CA2006/00474, Jun. 5, 2006, 10 pages.

* cited by examiner

SURGICAL TOURNIQUET APPARATUS FOR MEASURING LIMB OCCLUSION PRESSURE

FIELD OF THE INVENTION

This invention pertains to pneumatic tourniquet systems commonly used for stopping the flow of arterial blood into a portion of a surgical patient's limb to facilitate the performance of a surgical procedure, and for facilitating intravenous regional anesthesia. In particular, this invention pertains to pneumatic tourniquet apparatus for measuring the minimum pressure that must be applied to stop arterial blood flow into the portion of the limb to facilitate surgery

BACKGROUND OF THE INVENTION

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes an inflatable portion, and the inflatable portion of the cuff is connected pneumatically through one or two cuff ports by flexible plastic tubing to a tourniquet instrument that includes a pressure regulator to maintain the pressure in the inflatable portion of the cuff, when applied to a patient's limb at a desired location, near a reference pressure that is above a minimum pressure required to stop arterial blood flow past the cuff during a time period suitably long for the performance of a surgical procedure. Many types of such pneumatic surgical tourniquet systems have been described in the prior art, such as those described by McEwen in U.S. Pat. No. 4,469,099, U.S. Pat. No. 4,479,494, U.S. Pat. No. 5,439,477 and by McEwen and Jameson in U.S. Pat. No. 5,556,415 and U.S. Pat. No. 5,855,589.

To achieve better overall safety and performance, and in particular to achieve greater speed and accuracy in controlling the pressure in the tourniquet cuff, some advanced tourniquet systems include tourniquet cuffs that have two separate pneumatic cuff ports, so that two separate pneumatic passageways can be established between the inflatable portion of the cuff and the tourniquet instrument, by separately connecting flexible plastic tubing between each port and the instrument. Such systems are often called dual-port tourniquet systems. In one such dual-port tourniquet system of the prior art, described in U.S. Pat. No. 4,469,099, the pneumatic pressure regulation elements within the tourniquet instrument communicate pneumatically with the inflatable portion of the cuff through one port, and a pressure sensor within the tourniquet instrument communicates pneumatically with the inflatable portion of the cuff through the second port. This configuration enables more accurate sensing, monitoring and regulation of the actual pressure in the inflatable portion of the cuff that encircles the patient's limb, in comparison to single-port tourniquet systems. In a typical single-port tourniquet system of the prior art, the tourniquet cuff has only one port and only one pneumatic passageway is established between the tourniquet cuff and the instrument. The actual cuff pressure must be sensed indirectly, through the same tubing and port that is used to increase, decrease and regulate the pressure in the cuff during surgery. As a result, in such a single-port tourniquet system of the prior art, the accuracy and speed of pressure regulation, and the accuracy of the sensed cuff pressure, are affected by the pneumatic flow resistance within the single port and within the flexible plastic tubing that pneumatically connects the port and cuff to the tourniquet instrument.

Many studies published in the medical literature have shown that the safest tourniquet pressure is the lowest pressure that will stop the flow of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible.

It is well established in the medical literature that the optimal guideline for setting the pressure of a constant-pressure tourniquet is based on "Limb Occlusion Pressure" (LOP). LOP can be defined as the minimum pressure required, at a specific time in a specific tourniquet cuff applied to a specific patient's limb at a specific location, to stop the flow of arterial blood into the limb distal to the cuff. The currently established guideline for setting tourniquet pressure based on LOP is that an additional safety margin of pressure is added to the measured LOP, to account for physiologic variations and other changes that may be anticipated to occur normally over the duration of a surgical procedure.

Surgical staff can measure LOP manually by detecting the presence of arterial pulsations in the limb distal to a tourniquet cuff as an indicator of arterial blood flow past the cuff and into the distal limb. Such arterial pulsations can be defined as the rhythmical dilation or throbbing of arteries in the limb distal to the cuff due to blood flow produced by regular contractions of the heart. Detecting blood flow thus can be done using palpation, Doppler ultrasound or photoplethysmography to measure arterial pulsations. One technique for manual measurement of LOP based on monitoring arterial pulsations as an indicator of arterial blood flow is as follows: tourniquet cuff pressure is increased by an operator slowly from zero while monitoring arterial pulsations in the limb distal to the cuff until the pulsations can no longer be detected; the lowest tourniquet cuff pressure at which the pulsations can no longer be detected can be defined as the ascending LOP. A second manual technique is that an operator can slowly decrease tourniquet cuff pressure while monitoring to detect the appearance of arterial pulsations distal to the cuff; the highest pressure at which arterial pulsations are detected can be defined as the descending LOP. The accuracy of such manual measurements of LOP is very dependent on the sensitivity, precision and noise immunity of the technique for detecting and monitoring arterial pulsations, and on operator skill, technique and consistency. Under the best circumstances considerable elapsed time is required on the part of a skilled, experienced and consistent operator, using a sensitive and precise technique for detecting and monitoring pulsations as an indicator of distal blood flow, to accurately measure LOP by manual means.

Some surgical tourniquet systems of the prior art include means to measure LOP automatically. Prior-art tourniquet apparatus having automatic LOP measurement means are described by McEwen in U.S. Pat. No. 5,439,477 and by McEwen and Jameson in U.S. Pat. No. 5,556,415. Such prior-art systems have included blood flow transducers that employ a photoplethysmographic principle to sense blood flow in the distal limb, although other transducers have been suggested in the prior art to measure blood flow based on other principles. A blood flow transducer employing the photoplethysmographic principle uses light to indicate the volume of blood present in a transduced region, consisting of a combination of a residual blood volume and a changing blood volume resulting from arterial pulsations. An additional pressure margin based on recommendations in published surgical literature is added to the automatically measured LOP to provide a "Recommended Tourniquet Pressure" (RTP), as a guideline to help the surgical staff select the lowest tourniquet pressure that will safely stop arterial blood flow for the duration of a surgical procedure. Such prior-art systems allow the surgical staff to select the RTP, based on LOP, as the tourniquet pressure for that patient or to select another pressure based on the physician's discretion or the protocol at the institution where the surgery is being performed.

Despite their potential to recommend near-optimal settings of surgical tourniquet pressures for individual patients, prior-art surgical tourniquet systems that include means for automatic measurement of LOP have demonstrated limitations of performance that have prevented their widespread acceptance and routine use. The limitations are primarily in four areas: safety, probability of successful LOP measurement, speed of LOP measurement, and accuracy of LOP measurement.

Regarding safety, it is desirable during LOP measurement that the tourniquet cuff pressure not rise significantly above the pressure required to stop blood flow past the cuff for a significant period of time. This is because it is well established that the possibility of tourniquet-related injuries increases if tourniquet cuff pressure increases substantially. For this reason, prior-art tourniquet apparatus that measures LOP by descending from a high cuff pressure are considered to be less desirable than tourniquet apparatus that measures LOP by ascending from a low pressure. Also regarding safety, it is desirable that LOP measurements be made as quickly as possible, while still assuring that the resulting LOP measurement is sufficiently accurate to allow setting the tourniquet pressure based on the measured LOP. Speed of LOP measurement is desirable for three reasons related to safety and performance: first, it is well established that longer tourniquet times are associated with a higher possibility of tourniquet-related injuries; second, during LOP measurement, if venous outflow of blood from the limb is restricted by a pressurized tourniquet cuff for an excessively long period of time, then pooling of blood in the distal limb from arterial inflow may occur, possibly leading to passive congestion of the limb from residual blood that may be hazardous; and third, any continuing increase of residual blood in the distal limb over an extended measurement period may lead to measurement error in photoplethysmographic blood flow transducers, because such transducers inherently provide one indication of the combination of residual blood volume and varying blood volume resulting from arterial pulsations in the transduced portion, thus lengthening the time for successful completion of LOP measurement, or making successful LOP measurement impossible.

Experience with manual LOP measurement, and with prior-art tourniquet apparatus having LOP measurement capability, has shown that it is not possible in practice to measure the LOP of all patients. This is because the quality and magnitude of arterial blood flow measured by a blood flow transducer distal to the tourniquet cuff may not be sufficient in some patients for measurement or analysis, due to a variety of anatomic and physiologic factors. For such patients, the physician must revert to a standard tourniquet pressure setting based on the physician's discretion. No prior-art tourniquet system includes means to characterize the quality and magnitude of blood flow distal to the tourniquet cuff measured by a blood flow transducer, in order to quickly identify those patients and situations in which LOP measurement is unlikely to be successfully completed. As a result, considerable time may be taken in the surgical setting in an attempt to measure LOP which is ultimately unsuccessful as well as time-consuming.

Even for patients in whom LOP measurement is possible, the time required by tourniquet systems known in the prior art to successfully complete automatic LOP measurements may be considerable. In addition to the safety-related considerations described above, the extended time required for LOP measurement by prior-art tourniquet systems may significantly disrupt or delay normal activities in the operating room, and thus affect the efficiency of surgery. This is in part because the patient's operative limb must remain motionless during the measurement period, to avoid the introduction of variations in pneumatic cuff pressure and the introduction of noise due to movement of the distal blood flow transducer relative to the limb. In prior-art apparatus for measuring LOP, the reference pressure for the tourniquet cuff is typically increased from zero in many predetermined increments of increasing pressure. After each such predetermined increment or step of the reference pressure, time is required to allow the actual increased pressure within the tourniquet cuff to stabilize before measurements can be taken from the distal blood flow transducer and related to actual cuff pressure. Substantially increasing the predetermined step size in such prior-art systems might increase the speed of LOP determination, but could also decrease the accuracy of LOP measurement significantly. Thus the total time required for sufficiently accurate LOP measurement in prior-art systems can be substantial, and includes the time required to increase the reference pressure in many predetermined steps from zero, the time required to allow the actual cuff pressure to stabilize after each step, and the time required to take a measurement from the distal blood flow transducer at each step, until a LOP measurement is successfully made or until an arbitrary maximum pressure limit is reached without LOP being measured.

The accuracy of LOP measurements by prior-art tourniquet apparatus may be affected by two additional sources of error. First, because of the substantial time periods often required to measure LOP by prior-art tourniquet apparatus, error may be introduced into the LOP measurement due to accumulation of residual blood in the limb distal to the tourniquet cuff. This gradual accumulation of residual blood due to blocking of venous outflow by the tourniquet cuff can reduce the magnitude of the pulsations in blood volume that are associated with the rhythmical dilation or throbbing of the distal arteries over the duration of each cardiac cycle, from heartbeat to heartbeat. Also, such an increasing volume of residual blood in the distal limb during a measurement interval can cause a gradual change in the mean blood flow signal from a photoplethysmographic transducer during the period, for reasons described above. Such a gradual change may make valid arterial pulsations indicating arterial blood flow difficult or impossible to detect, and reduces the maximum possible amplification of the signal from the distal blood flow transducer, thus reducing the accuracy of subsequent analysis. A second source of error in LOP measurement by prior-art tourniquet apparatus results from movement of the patient's limb and movement of the distal blood flow transducer relative to the attached limb, either of which could mask valid arterial pulsations indicating blood flow or could be misinterpreted as valid arterial pulsations.

There is a need for improved surgical tourniquet apparatus for measuring LOP, to overcome the above-described limitations of prior-art tourniquet systems, so that such apparatus will be suitable for routine use in all surgical procedures involving a tourniquet. To be routinely useful in this context, apparatus for measuring LOP automatically should not introduce secondary hazards associated with the measurement of LOP, should have a high probability of successful completion after LOP measurement is initiated, should complete LOP measurement sufficiently fast so that the measurement of LOP does not disrupt or unduly delay normal activities in the operating room, and should result in an LOP measurement that is accurate within surgically acceptable expectations so that it can be used as the basis for optimal setting of tourniquet pressure. The present invention addresses the need for improved surgical tourniquet apparatus for measuring LOP.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Hardware

Figure 1:
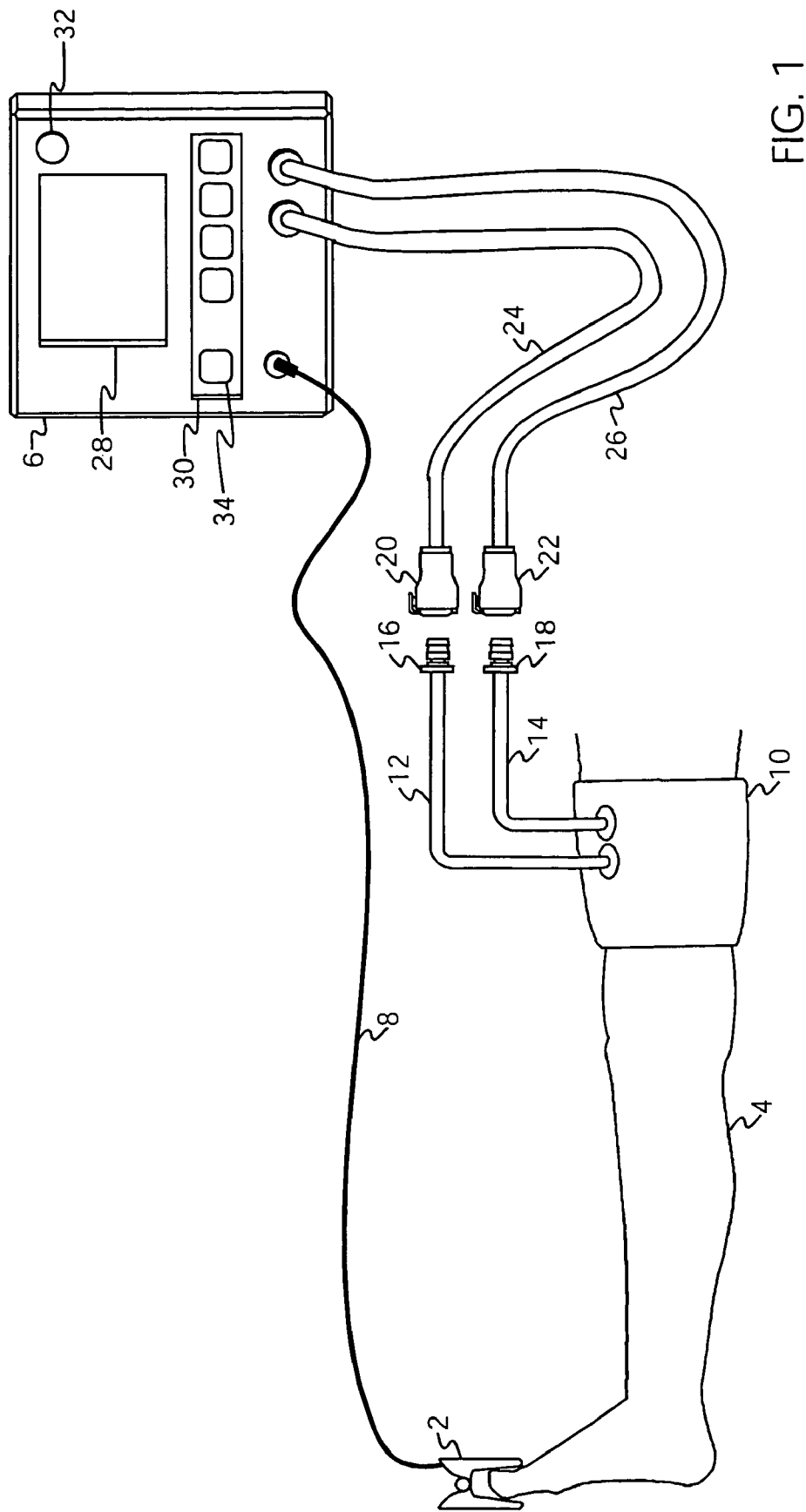
FIG. 1 is a pictorial representation of the preferred embodiment in a surgical application.

FIG. 1 shows blood flow transducer 2 applied to a digit of patient limb 4 and connected to instrument 6 via multi-conductor shielded cable 8. Blood flow transducer 2 is positioned on patient limb 4 at a location that is distal to pressurizing cuff 10 which is also shown applied to patient limb 4. This configuration permits blood flow transducer 2 to detect blood flow in patient limb 4 and changes in blood flow that occur in patient limb 4 as a result of the pressurization of cuff 10. Blood flow transducer 2 is used by instrument 6 when instrument 6 is performing automatic measurements of limb occlusion pressure (LOP). LOP has been defined above to be the minimum pressure required, at a specific time in a specific tourniquet cuff applied to a specific patient's limb at a specific location, to stop the flow of arterial blood into the limb distal to the cuff.

Cuff 10 is pneumatically connectable to instrument 6. The inflatable portion of pressurizing cuff 10 has two separate pneumatic connections and is generally similar in design and construction to the cuffs described by McEwen in U.S. Pat. No. 5,741,295, No. 5,649,954, No. 5,484,831 and by Robinette-Lehman in U.S. Pat. No. 4,635,635. Cuff 10 is adapted for use in a sterile surgical field in an operating room environment by being formed of materials that can withstand, and that can be sterilized by, techniques normally used to sterilize medical devices to a level of sterility that allows them to be safely used within a sterile surgical field. Cuff 10 is a dual-port cuff, and separate pneumatic passageways to the inflatable portion of cuff 10 are provided by cuff port 12 and cuff port 14 so that each passageway is independent of the other. In FIG. 1 cuff port 12 and cuff port 14 are of sufficient length to allow pneumatic connections to cuff 10 to be made outside of a sterile surgical field. Cuff port 12 and 14 are fitted with male locking connectors 16 and 18 (DSM2202, Colder Products Company, St. Paul, Minn.) respectively, and mate to form releasable pneumatic connections with female locking connectors 20 and 22 (PMC1704, Colder Products Company, St. Paul, Minn.). For clarity, the connectors illustrated in FIG. 1 are shown disconnected; in the following description of the preferred embodiment the connectors are mated and form part of the pneumatic passageways between instrument 6 and cuff 10. Pneumatic connections from instrument 6 to cuff 10 are made by flexible plastic tubing 24 and 26 which are fitted with female locking connectors 20 and 22 respectively.

As can be seen in FIG. 1, instrument 6 has a user interface consisting of graphic display panel 28, keypad 30, and visual alarm indicator 32. Display panel 28 is employed for the selective display of any of the following alphanumeric information: limb occlusion pressures and recommended tourniquet pressures as measured and calculated by instrument 6; actual cuff pressures as measured by instrument 6; reference or "set" cuff pressure levels, alarm reference "limits" or values; alphanumeric alarm messages describing detected alarm conditions and other information required for the operation of instrument 6.

Keypad 30 provides a means for a user of instrument 6 to control the operation of instrument 6. Keypad 30 includes a limb occlusion pressure measurement (LOP) key 34, which when depressed will initiate the measurement of LOP as described further below. Keypad 30 also has an "inflate" key to initiate the inflation of cuff 10, a "deflate" key to initiate the deflation of cuff 10, and other keys to permit the user of instrument 6 to adjust the reference pressure level and set inflation time alarm limits.

Visual alarm indictor 32 is a bright red light emitting diode (LED) which is activated by instrument 6 in response to detected alarm conditions. Instrument 6 also signals the presence of an alarm condition by generating an audible tone to further alert the user to the presence of an alarm condition and displays alarm text messages describing the alarm condition on display panel 28. One example of a detected alarm condition that requires the user's attention is the accidental removal of blood flow transducer 2 during a limb occlusion pressure measurement.

Figure 2:
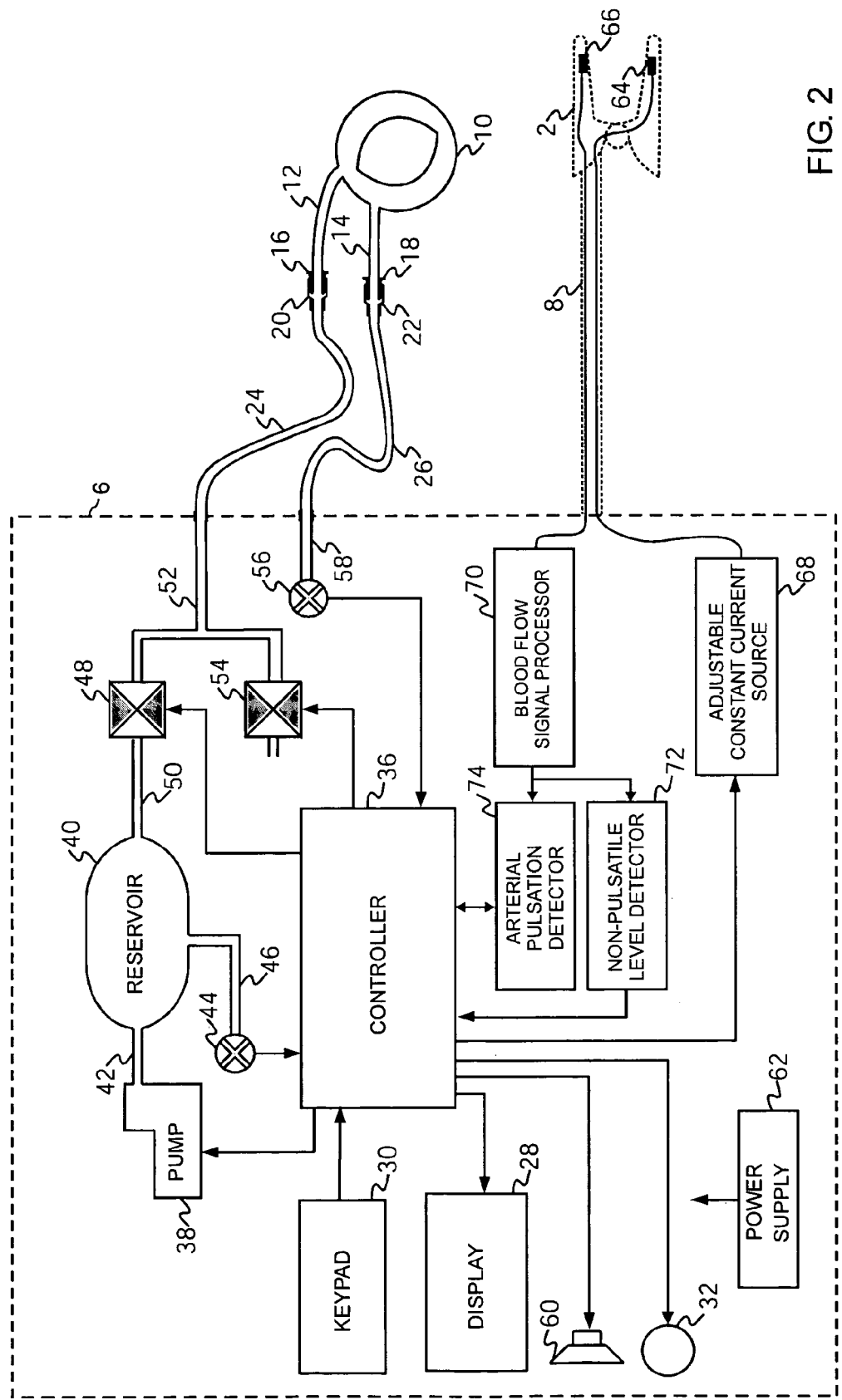
FIG. 2 is a block diagram of the preferred embodiment.

Referring to the block diagram of instrument 6 shown in FIG. 2, controller 36 comprises a microcontroller (MC68HC16Z1, Freescale Semiconductor, Austin, Tex.), associated memory and control software, analog and digital peripheral interface circuitry, and other necessary support components.

As shown in FIG. 2, pneumatic pump 38 (KNF Neuberger, Inc., Trenton, N.J.) is pneumatically connected to reservoir 40 by tubing 42. In response to control signals from controller 36, pump 38 operates to pressurize reservoir 40. Reservoir pressure transducer 44 is pneumatically connected by tubing 46 to reservoir 40 and generates a reservoir pressure signal. The reservoir pressure signal is communicated to controller 36. Controller 36 acts to maintain the pressure in reservoir 40 near a reservoir pressure level. Controller 36 sets the reservoir pressure level to a pressure above the reference pressure level set by the user of instrument 6 or automatically by controller 36 during a limb occlusion pressure measurement; the reservoir pressure level is set to a level significantly greater than the reference pressure level, typically 100 mmHg. Controller 36 in response to the reservoir pressure level and the reservoir pressure signal activates pump 38 to maintain the level of the reservoir pressure signal near the reservoir pressure level.

Inflation valve 48 (EVO-3-12V, Clippard Instrument Laboratory, Cincinnati, Ohio) is configured as a two position normally closed valve. One side of the valve is pneumatically connected via tubing 50 to reservoir 40 the other side of the valve is connected to cuff 10 via the pneumatic passageway formed by manifold 52, tubing 24, connectors 20 and 16 and cuff port 12. When energized by controller 36, inflation valve 48 moves to the open position and allows pressurized gas to flow from reservoir 40 to cuff 10, thereby increasing the pressure of gas in the inflatable portion of cuff 10.

Deflation valve 54 (EVO-3-12V, Clippard Instrument Laboratory, Cincinnati, Ohio) is configured as a two position normally closed valve. One side of the valve is pneumatically connected to cuff 10 via the pneumatic passageway formed by manifold 52, tubing 24, connectors 20 and 16 and cuff port 12, the other side is open to atmosphere. When energized by controller 36, deflation valve 54 moves to the open position and allows pressurized gas to flow from cuff 10 to atmosphere, thereby decreasing the pressure of gas in the inflatable portion of cuff 10.

In the preferred embodiment the inflation and deflation valves share a common pneumatic connection with a port of cuff 10. It will be appreciated that other configurations of the inflation and deflation valves may be employed. For example, it may be desirable to have the inflation valve communicate separately with one port of cuff 10 and to have the deflation valve communicate separately with the other port of cuff 10. This possible configuration may be desirable if the inflatable portion of cuff 10 includes a pressure transducer that communicates wirelessly with instrument 6 to directly indicate the pressure in cuff 10.

Cuff pressure transducer 56 is pneumatically connected to cuff 10 via the pneumatic passageway formed by tubing 58, tubing 26, connectors 22 and 18 and cuff port 14 and generates a cuff pressure signal which is communicated to controller 36. The separate independent pneumatic connection between the inflatable portion of cuff 10 and cuff pressure transducer 56 provides for an accurate indication of the actual pressure of gas within cuff 10 at any time. Controller 36 is able to resolve changes in the cuff pressure signal as small as 0.15 mmHg.

As noted above, controller 36 will, in response to generated alarm signals alert the user of an alarm condition by activating visual alarm indicator 32 and producing audible tones. Speaker 60 is connected to controller 36, and electrical signals having different frequencies to specify different alarm signals and conditions are produced by controller 36 and converted to audible sound by loudspeaker 60.

Power supply 62 connects to an external AC supply and provides regulated DC power for the normal operation of all electronic components of instrument 6. Power supply 62 may also include a battery to enable instrument 6 to continue to operate in the absence of an external AC supply.

Pressure Regulation

A user of instrument 6 may use keypad 30 to select a reference pressure level; this is the pressure of gas that instrument 6 will attempt to maintain in the inflatable portion of cuff 10 when cuff 10 is inflated. Controller 36 will generate high or low pressure alarm signals if the pressure in cuff 10 cannot be maintained near the selected reference pressure level. If the cuff pressure level exceeds the reference pressure level by 15 mmHg a high pressure alarm signal will be generated by controller 36. If the cuff pressure level falls below the reference pressure level by 15 mmHg a low pressure alarm signal will be generated by controller 36.

When controller 36 detects that the "inflate" key on keypad 30 has been depressed by a user of instrument 6, controller 36 operates to inflate cuff 10 to a pressure near the selected reference pressure level and to then regulate the pressure in cuff 10 near the reference pressure level until such time that controller 36 detects that the "deflate" key on keypad 30 has been depressed by a user of instrument 6. Controller 36 may also inflate, adjust the reference pressure level, and deflate cuff 10 automatically during a limb occlusion pressure measurement as described further below.

To inflate and regulate the pressure in cuff 10 controller 36 includes a pressure regulator; the pressure regulator in the preferred embodiment is implemented as a control algorithm that operates as described below. At regular predetermined regulation intervals of 40 ms controller 36 computes a pressure error signal. The pressure error signal corresponds to the difference between the reference pressure level and the cuff pressure level. Controller 36 uses the pressure error signal as a term in a proportional integral control algorithm to calculate activation time intervals for inflation valve 48 and deflation valve 54. To increase the gas pressure in cuff 10 when the cuff pressure signal is below the reference pressure level, the activation time interval for deflation valve 54 is set to zero and the activation time interval for inflation valve 48 is proportional to the magnitude of the pressure error signal and the integral of the pressure error signal. To decrease the gas pressure in cuff 10 when the cuff pressure signal is above the reference pressure level, the activation time interval for inflation valve 48 is set to zero and the activation time interval for deflation valve 54 is proportional to the magnitude of the pressure error signal and the integral of the pressure error signal. Controller 36 limits the maximum valve activation time intervals of valve 48 and valve 54 to the regulation interval time (40 ms). It will be appreciated by those skilled in the art that alternate pressure regulation algorithms could be employed to control the activation of inflation valve 48 and deflation valve 54 in response to a cuff pressure signal and a reference pressure level, or that proportional valves could be used instead of the valves used in the preferred embodiment. Also it will be appreciated that a regulator has a response time, consisting of the amount of time required for the pressure of gas in the cuff to reach the level of the reference pressure level after a new reference pressure level has been selected. The regulator response time will depend upon the magnitude of the change in reference pressure level, the volume of cuff 10 and the characteristics of the pneumatic components in instrument 6 and the specifics of the control algorithm used. Thus the actual pressure of gas in cuff 10 may differ substantially from the reference pressure level for a varying period of time after a change in the reference pressure level.

In order to correctly regulate the pressure of gas in cuff 10 at a pressure near the cuff pressure reverence level and correctly indicate over and under pressure alarm conditions, controller 36 must have available an accurate indication of the pressure within the inflatable portion of cuff 10. In the preferred embodiment the accurate measurement of the pressure of gas in cuff 10 is facilitated by cuff pressure transducer 56 and the direct pneumatic connection between the inflatable portion of cuff 10 and transducer 56. The connection between the inflatable portion of cuff 10 and transducer 56 is made by tubing 58, flexible plastic tubing 26, connectors 22 and 18, and cuff port 14. An accurate measurement of the pressure of gas in cuff 10 at any time is also critical to the ability of instrument 6 to accurately and rapidly measure LOP, as explained below.

Blood Flow Transducer and Signal Processing

Referring again to FIG. 2, the internal components of blood flow transducer 2 are shown in detail. Blood flow transducer 2 of the preferred embodiment employs the principle of photoplethysmography and is adapted for positioning on the limb distal to the tourniquet cuff, although it will be appreciated that other types of blood flow transducers employing other principles may be used, and it will be appreciated that some types of blood flow transducers may be physically integrated into the structure of a tourniquet cuff. In the preferred embodiment, blood flow transducer 2 has a hinged plastic housing that is configured for application to a digit of a limb. Blood flow transducer 2 may be applied to a finger or thumb of the hand or a toe of the foot. Transducer 2 includes an infrared light emitting diode (IRLED) 64 and a photodiode 66 which is sensitive to the wavelength of light emitted by IRLED 64. In the preferred embodiment an IRLED with a wavelength of 915 nm is employed. Within blood flow transducer 2 IRLED 64 and photodiode 66 are positioned directly opposite each other such that light emitted by IRLED 64 is readily detected by photodiode 66. When applied to a digit IRLED 64 illuminates a volume of tissue and photodiode 66 detects the light that is transmitted through this volume of tissue.

IRLED 64 is connected via multi-conductor cable 8 to adjustable constant current source 68. The intensity of light emitted by IRLED 64 is proportional to the amount of electrical current that flows through IRLED 64. Controller 36 communicates with adjustable constant current source 68 to set the level of current that flows through IRLED 64 and thereby the intensity of light emitted by IRLED 64. In the preferred embodiment the current source 68 can be adjusted to supply electrical current ranging from 0 to 100 milliamps in steps of 0.1 milliamps by controller 36.

Photodiode 66 generates an electrical current that is linearly proportional to the intensity of light that strikes the light sensitive area of photodiode 66. Photodiode 66 is connected by multi-conductor cable 8 to blood flow signal processor 70. Signal processor 70 amplifies, filters, and digitizes the current generated by photodiode 66 to produce a blood flow signal that is representative of the intensity of light that strikes photodiode 66. The characteristics of photodiode 66 and the electronic circuits within signal processor 70 determine the minimum and maximum light intensities that the blood flow signal can represent. As described below, the preferred embodiment operates to maintain the level of the blood flow signal within the dynamic range of signal processor 70.

Figure 3:
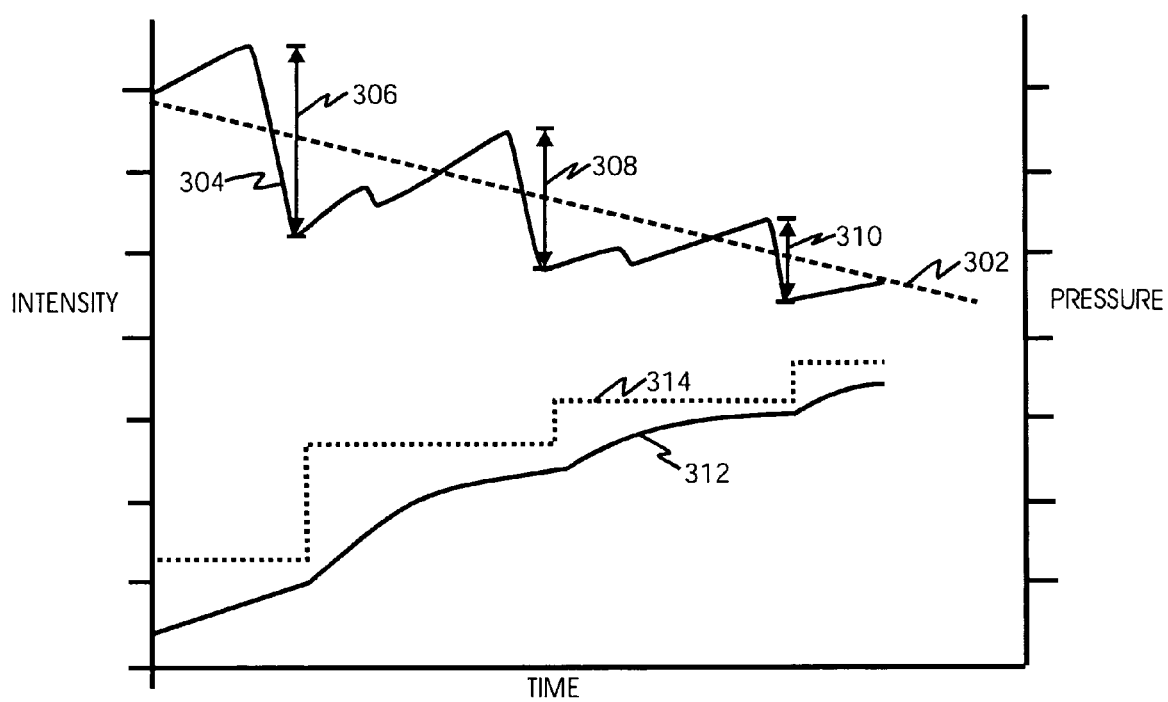
FIG. 3 is an illustration that shows increases in the level of the cuff reference pressure in synchrony with arterial pulsations detected during the measurement of limb occlusion pressure by the preferred embodiment.

When blood flow transducer 2 is applied to a digit of a patient's limb the intensity of light reaching photodiode 66 is dependent upon a number of factors. These factors are the initial intensity of the light emitted by IRLED 64; the amount of light absorbed by the skin pigmentation, tissue and bone of the digit; the amount of light absorbed by venous blood and non-pulsatile arterial blood and pulsatile arterial blood; and the optical path length between IRLED 64 and photodiode 66. When cuff 10 is deflated, a relatively constant amount of light is absorbed by the skin pigmentation, bone other tissue, venous blood and the non-pulsatile part of the arterial blood. This aggregate non-pulsatile component of the blood flow signal, illustrated as non-pulsatile signal 302 in FIG. 3, is detected and measured by non-pulsatile level detector 72. Non-pulsatile level detector 72 communicates to controller 36 the level of non-pulsatile signal 302.

During each cardiac cycle the diameters of the arteries and arterioles alternately increase and decrease in response to arterial blood flow pulsations. This alternating increase and decrease in diameters affects the optical path length between IRLED 64 and photodiode 66 and produces a rhythmical and alternating variation in the intensity of light transmitted through the digit that is in synchrony with each cardiac cycle. Typically, this rhythmical and alternating variation of intensity is 1-2 percent of the total amount of light transmitted through the volume of tissue, and results in the production by signal processor 70 of a blood flow signal having alternating variations as illustrated in FIG. 3. Arterial pulsation detector 74 detects an arterial pulsation by detecting the occurrence of the alternating variation in the blood flow signal from signal processor 70 that occurs during each cardiac cycle, and further determines the relative magnitude of each detected arterial pulsation by determining the difference between the minimum and maximum of each alternating variation of the blood flow signal, as illustrated in FIG. 3.

FIG. 3 illustrates non-pulsatile signal 302, blood flow signal 304, and arterial pulsations of magnitudes 306, 308 and 310 that decrease as cuff pressure 312 increases in response to increases in reference pressure level 314. FIG. 3 also illustrates that cuff pressure 312 may differ significantly from reference pressure level 314 for varying periods of time after changes in reference pressure level 314. Finally, FIG. 3 illustrates that, in the preferred embodiment, changes in reference pressure level 314 are only made in synchrony with arterial pulsations detected by arterial pulsation detector 74, as explained further below. Synchronizing any change in reference pressure level 314 to detected arterial pulsations is an important characteristic of the preferred embodiment that greatly increases the speed of LOP measurement in comparison to prior-art apparatus in which increases in reference pressure levels are made at arbitrary, unsynchronized times.

The magnitude is affected by the intensity of light emitted by IRLED 64. Generally, as the intensity of light emitted by IRLED 64 increases, the volume of tissue illuminated by IRLED 64 increases which results in an increase in the magnitude of the alternating and rhythmical variation of the blood flow signal as more arteries and arterioles are illuminated in the optical path between IRLED 64 and photodiode 66.

The optical path length through the volume of tissue between IRLED 64 and photodiode 66 is also affected by any change in diameter of the venules and the amount of venous blood in the tissue. When cuff 10 is pressurized to a level that is greater than that required to occlude venous blood from flowing out of the limb but still at a level that allows arterial blood to flow into the limb there is an increase in the volume of venous blood present in the limb and a corresponding increase in the diameter of the venules. This increase in diameter increases the optical path length through the volume of tissue and results in a decrease in the amount of light detected by photodiode 66. This decrease in light intensity happens gradually, but may be substantial, resulting in reductions of up to three orders of magnitude of the light transmitted through the volume of tissue. In the preferred embodiment this change in the intensity of light transmitted through the volume of tissue is compensated for by an increase in the intensity of IRLED 64, as described further below. In some circumstances described further below it may not be possible to compensate for this magnitude of change in intensity as IRLED 64 has an upper limit to the intensity of light that it can produce.

Each cardiac cycle that occurs when cuff 10 is at a pressure that partially or completely stops venous outflow, but not arterial inflow, results in an increase in the amount of venous blood in the volume of tissue illuminated by IRLED 64. It is important to minimize the time that cuff 10 is at these pressures because the accumulation of venous blood may be hazardous, as explained above. It is also important that this time be minimized to insure that the photoplethysmographic blood flow signal remains in a region that is within the dynamic range of IRLED 64 to illuminate the tissue, and within the dynamic range of the electronic circuits used to detect and process the signal from photodiode 66. The preferred embodiment acts to minimize the time that cuff 10 is at these pressures when attempting to make a measurement of LOP by assessing during an initialization period whether such an attempted measurement is likely to be successful, as follows. In the initialization period, if a blood flow signal cannot be detected by signal processor 70, or if alternating rhythmical variations of the blood flow signal characterizing arterial pulsations above a predetermined minimum initial magnitude cannot be detected by arterial pulsation detector 74, then controller 36 increases the intensity of IRLED 64 by adjusting the current to IRLED 64 by means of adjustable constant current source 68 in an effort to increase the magnitude of the blood flow signal to a level suitable for analysis. If this adjustment by current source 68 still does not result in a blood flow signal having variations greater than the predetermined minimum initial magnitude, then controller 36 promptly terminates the attempt to measure LOP and produces an appropriate indication perceptible to the operator. In this way, the preferred embodiment minimizes the duration of an attempt to measure LOP that may delay the start of surgery, and that may cause venous blood pooling, if that measurement of LOP is unlikely to be successfully completed, and allows the operator to promptly select another reference pressure level for the tourniquet system that is not based on LOP.

If an attempt to measure LOP has not been terminated during the initialization period, arterial pulsation detector 74 continues to analyze the blood flow signal from signal processor 70 to detect the occurrence of each alternating rhythmical variation above a minimum detection threshold that characterizes an arterial pulsation of blood flow, and to indicate to controller 36 the magnitude of the difference between the maximum and minimum of the alternating rhythmical variation, as illustrated by magnitudes 306, 308 and 310 in FIG. 3. Each magnitude is representative of the amount of arterial blood flowing into the volume of tissue between IRLED 64 and photodiode 66 during the period of each cardiac cycle. To be correctly identified as an arterial pulsation of blood flow, the magnitude must exceed the minimum detection threshold. The minimum detection threshold of arterial pulsation detector 74 is initially set to a predetermined threshold, and may subsequently be set by controller 36 to another threshold.

When an arterial pulsation is detected by arterial pulsation detector 74, the time of occurrence is communicated to controller 36, and pulsation detector 74 enters a refractory time period immediately after the detected occurrence. During the refractory time period, pulsation detector 74 is non-responsive to the blood flow signal from signal processor 70. This non-responsiveness of pulsation detector 74 to the blood flow signal during the refractory time period allows controller 36 to make adjustments to the level of the current supplied by adjustable constant current source 68 to IRLED 64 while preventing pulsation detector 74 from erroneously analyzing any noise or artifact in the blood flow signal resulting from the adjustments to the level of current to IRLED 64. During the measurement of LOP, controller 36 typically sets the refractory time period of pulsation detector 74 to be equal to 75 percent of the time between successively detected arterial pulsations. Depending on the time between successive pulsations, the duration of the refractory time period may be adjusted by controller 36 from a predetermined initial time of 350 milliseconds to a predetermined maximum time of 1200 milliseconds.

Limb Occlusion Pressure Measurement

To automatically measure the limb occlusion pressure, controller 36 must determine the minimum pressure required in cuff 10 to prevent arterial blood flow into patient limb 4 distal to the location of cuff 10. As described in detail below, controller 36 does this by analyzing signals produced by non-pulsatile level detector 72, by arterial pulsation detector 74 and by blood flow signal processor 70 while increasing the pressure in cuff 10 to a pressure level at which arterial blood flow is no longer detectable above a minimum detection threshold.

Figure 4:
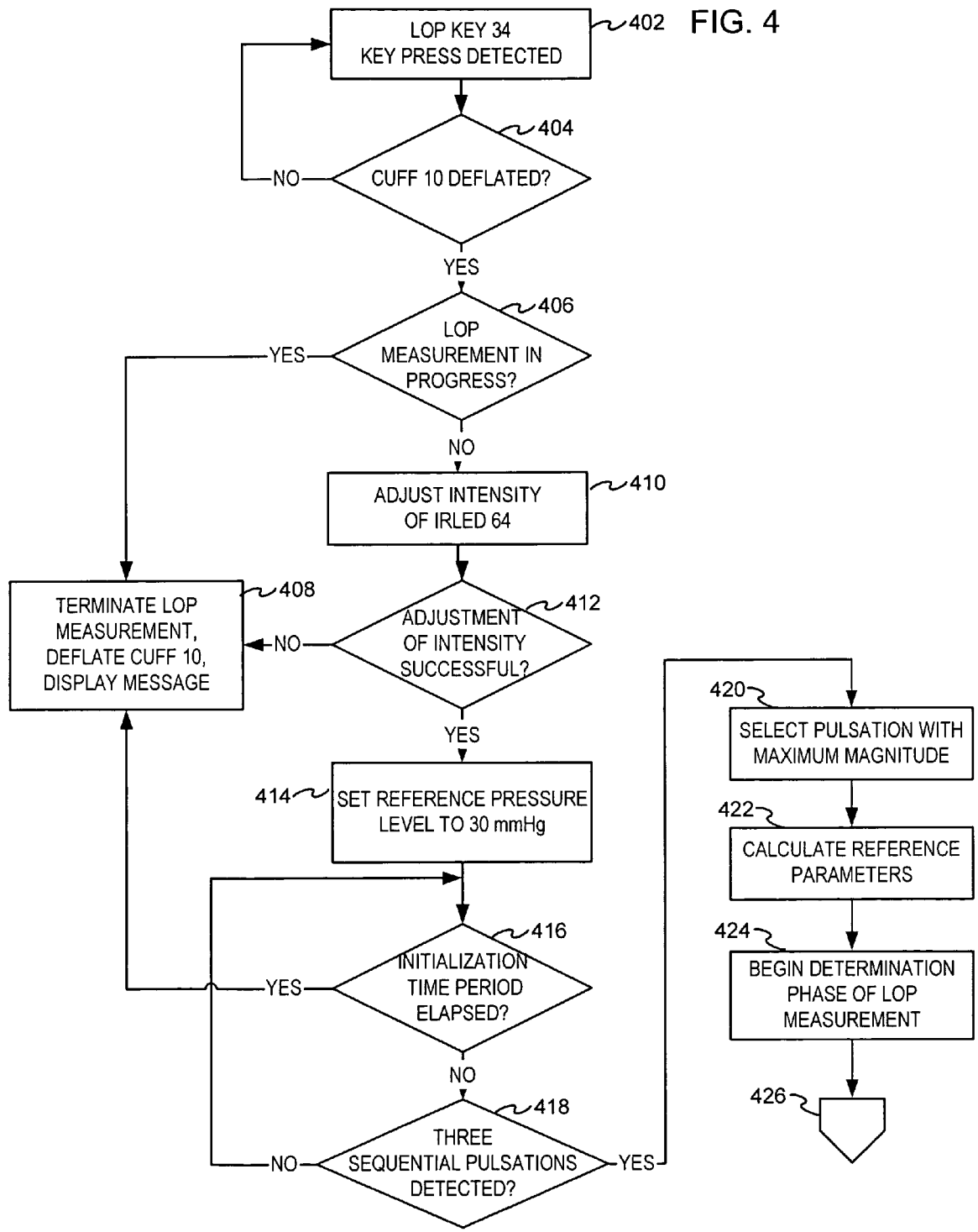
FIG. 4 and FIG. 5 are flow charts depicting the sequence of operations performed by the preferred embodiment during measurement of limb occlusion pressure.
Figure 5:
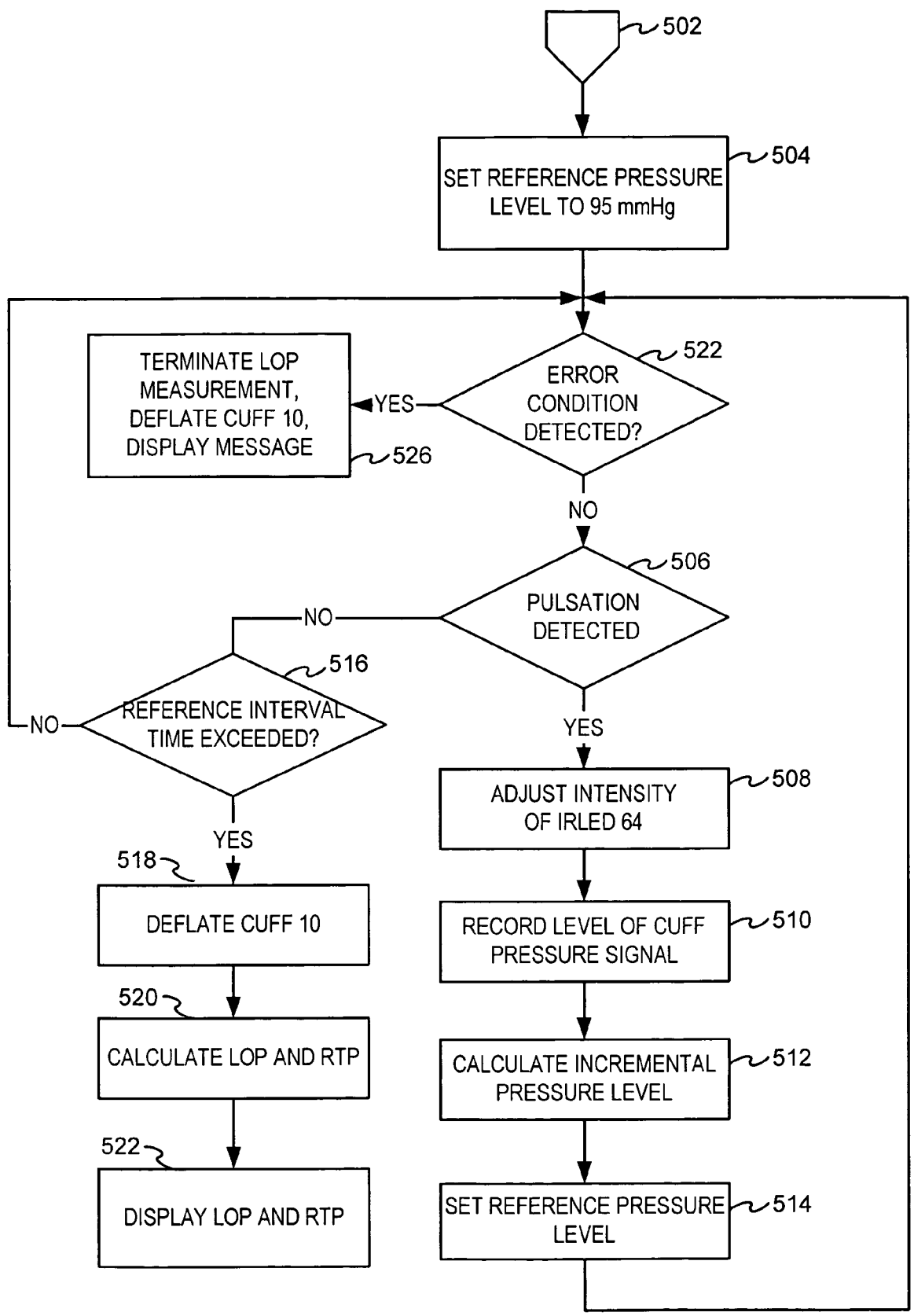

To enable a better understanding of the sequence of operations completed and decisions made by controller 36 during the automatic measurement of limb occlusion pressure a flow chart is provided in FIG. 4 and FIG. 5.

Referring to the flow chart in FIG. 4, when controller 36 detects that LOP key 34 on keypad 30 has been depressed (402) it first determines if cuff 10 is already inflated and being regulated as would be the case if a user of instrument had previously activated the inflate key on keypad 30 (404). Controller 36 only responds to LOP key 34 to initiate an LOP measurement sequence when cuff 10 is deflated and controller 36 is not regulating the gas pressure within cuff 10. This safety feature of the preferred embodiment prevents the user from inadvertently initiating a measurement of LOP at a time when a surgical procedure may be in progress.

If controller 36 detects that LOP key 34, or any other key on keypad 30 has been depressed while a LOP measurement sequence is in progress, controller 36 terminates the LOP measurement (406). An appropriate alarm message is shown on display panel 28 and controller 36 activates deflation valve 54 to vent gas from cuff 10 (408). This allows a user of instrument 6 to safely cancel an LOP measurement sequence that is in progress.

The LOP measurement sequence performed by controller 36 has two phases: an initialization phase during an initialization time period when reference parameters are established; and a determination phase during which the reference pressure level is monotonically increased until the pressure in cuff 10 reaches the limb occlusion pressure.

The initialization phase of the sequence for measuring LOP begins with controller 36 adjusting the intensity of IRLED 64 by communicating with constant current source 68 (410). The intensity of IRLED 64 is set to a level that produces a non-pulsatile photoplethysmographic signal at a level indicated by non-pulsatile level detector 72 that is near a predetermined initial target level.

If the non-pulsatile photoplethysmographic signal cannot be set to a level that is near the initial target level, such as may be the case if blood flow transducer 2 is applied to a very thick digit or a to digit that for other reasons absorbs a significant portion of the light emitted by IRLED 64 (412), controller 36 determines that the LOP measurement sequence is unlikely to successfully complete, terminates the measurement attempt, and displays an appropriate message on display panel 28 (408). Also, if the amount of current that is required from constant current source 68 to produce a non-pulsatile photoplethysmographic signal at a level near the initial target level exceeds a predetermined maximum, then controller 36 also determines that the LOP measurement sequence is unlikely to successfully complete because there will be insufficient adjustment range available to further increase the intensity of IRLED 64 to compensate for changes in venous blood volume that may occur during the measurement.

Next, controller 36 sets the reference pressure level to a predetermined initial level of 30 mmHg (414). The pressure regulator then commences inflation of cuff 10 to a pressure near 30 mmHg.

Controller 36 then waits for a predetermined maximum time period of 5 seconds (416) for arterial pulsation detector 74 to detect three sequential blood flow pulsations with a magnitude greater than a predetermined minimum initial magnitude (418). If three sequential pulsations that exceed the minimum initial magnitude are not detected within the predetermined maximum time period, indicating that the LOP measurement attempt is unlikely to be successfully completed, then the LOP measurement sequence is terminated and the reference pressure level is set to zero to start the deflation of cuff 10. A message is displayed on display panel 28 to alert the user that an LOP measurement could not be completed (408), thus minimizing the duration of an LOP measurement attempt that might be unsuccessful and that might delay the start of surgery and lead to excessive accumulation of venous blood.

If arterial pulsation detector 74 detects three sequential arterial blood flow pulsations that exceed the predetermined minimum initial magnitude, controller 36 calculates the levels of reference parameters to be used in the determination phase of the LOP measurement sequence. Controller 36 chooses from the three sequentially detected pulsations the pulsation with the greatest magnitude (420), and the magnitude of this pulsation is selected by controller 36 as the reference magnitude. As described below, controller 36 makes comparisons of the magnitude of subsequent pulsations to the reference magnitude. Controller 36 calculates a reference pulsation interval time which is the time interval between two of the three detected successive arterial pulsations (422). Controller 36 sets the refractory period of arterial pulsation detector 74 to 75 percent of the calculated reference pulsation interval time. Controller 36 also calculates the minimum detection threshold and communicates this threshold to arterial pulsation detector 74. As described above, the minimum detection threshold determines the minimum magnitude of an arterial pulsation that is detected by arterial pulsation detector 74. In the preferred embodiment, controller 36 computes the minimum detection threshold to be the greater of 5 percent of the reference magnitude and a predetermined minimum threshold.

Controller 36 next enters the determination phase of the LOP measurement sequence (424). The flow chart shown in FIG. 4 continues (426) in FIG. 5 (502). FIG. 5 depicts the determination phase of the LOP measurement sequence, controller 36 begins by setting the reference pressure level to a predetermined level of 95 mmHg (504). Controller 36 compensates for changes in the amount of venous blood present in the volume of tissue between IRLED 64 and photodiode 66 that may occur during the determination phase of the LOP measurement sequence as follows. Each time an arterial blood flow pulsation is detected by arterial pulsation detector 74 (506), controller 36 computes a new level for adjustable constant source 68 and thereby the intensity of IRLED 64. Controller 36 uses a proportional control algorithm to calculate a new level for constant current source 68 that maintains the level of the non-pulsatile photoplethysmographic signal from non-pulsatile level detector 72 near the target level set previously (508). The change to the intensity of IRLED 64 is made during the refractory period of arterial pulsation detector 74 so that artifacts that are caused by changing of the intensity of IRLED 64 do not affect arterial pulsation detector 74. By continuously updating the level of constant current source 68 after each arterial pulsation is detected in response to changes in the non pulsatile signal level, controller 36 can compensate for changes in the absorption of light emitted by IRLED 64 due to changes in the amount of venous blood present in the volume of tissue illuminated by IRLED 64 and maintain the non-pulsatile photoplethysmographic signal near the target level.

To increase the pressure in cuff 10 as rapidly as possible to the LOP, and at the same time to provide an accurate measurement of LOP, controller 36 operates as follows. Each time an arterial blood flow pulsation is detected by arterial pulsation detector 74 a new reference-pressure level is calculated by controller 36. Near the time that the pulsation is detected, controller 36 records the level of the cuff pressure signal (510); this represents the pressure of gas in cuff 10 near the time that the blood flow pulsation occurred. Based on the magnitude of the detected blood flow pulsation in comparison with the reference magnitude an incremental pressure level is calculated (512). Shortly after the detection of the blood flow pulsation and thus in synchrony with the pulsation, the reference pressure level is set by controller 36 to a level equal to the sum of the calculated incremental pressure level and the recorded cuff pressure level (514).

During the measurement of LOP, the magnitude of a detected arterial blood flow pulsation is dependent upon the pressure in cuff 10 at the time the pulsation occurs. As the pressure in cuff 10 nears the pressure required to totally occlude arterial blood flow, the magnitudes of arterial blood flow pulsations are reduced. To enable the preferred embodiment to rapidly increase the pressure in cuff 10 to the minimum pressure that occludes arterial blood flow, while not increasing the pressure in cuff 10 above that minimum pressure, the size of the pressure increment that is made after each detected arterial pulsation is dependent on the magnitude of the detected arterial blood flow pulsation. By making progressively smaller increments in pressure for cuff 10 as the cuff pressure nears the LOP, the preferred embodiment can make a very rapid and accurate determination of LOP.

In the preferred embodiment, the incremental pressure level is calculated as follows: 15 mmHg for a pulsation with a magnitude of 66 percent of the reference magnitude or greater; 10 mmHg for a pulsation with a magnitude of 50-65 percent of the reference magnitude; 7 mmHg for a pulsation with a magnitude of 33-49 percent of the reference magnitude; 5 mmHg for a pulsation with a magnitude of 20-32 percent of the reference magnitude; and 3 mmHg for a pulsation with a magnitude of less than 20 percent of the reference magnitude.

By making each increased reference pressure level equal to the sum of the calculated incremental pressure level that is based on the magnitude of an arterial pulsation plus the recorded cuff pressure level (510) at the time of that pulsation, and by increasing the reference pressure level in synchrony with that pulsation, the LOP measurement can proceed rapidly, accurately, and independently of the response time characteristic of the pressure regulator in combination with the pneumatic elements of the preferred embodiment. As an example, if the cuff pressure signal corresponds to a level of 133 mmHg when a pulsation is detected, and if the magnitude of the detected pulsation relative to the reference magnitude is greater than 66 percent, then controller 36 sets the reference pressure level to 148 mmHg (133+15) shortly after the pulsation. This is a more rapid and more accurate way to approach the true LOP in comparison to prior art apparatus in which each increased reference pressure level is typically determined by adding a predetermined increment to the previous reference pressure level, and in which the reference pressure level is increased only after sufficient time has elapsed to allow actual cuff pressure to reach the previous reference pressure level.

Referring again to FIG. 5, controller 36 continues to increase the reference pressure level each time a arterial blood flow pulsation is detected by arterial pulsation detector 74 until an arterial blood flow pulsation is not detected for a period of time that is two times the reference pulsation to pulsation interval time determined during the initialization phase of the LOP measurement sequence (516). When during the determination phase of the LOP measurement sequence an arterial blood flow pulsation is not detected for this period of time, controller 36 calculates the limb occlusion pressure to be the pressure of gas in cuff 10 as represented by the cuff pressure signal.

Controller 36 then deflates cuff 10 by setting the reference pressure level to zero and activating deflation valve 54 (518). Controller 36 then calculates the recommended tourniquet pressure as described below (520) and displays the results of the LOP measurement on display panel 28, this completes the LOP measurement sequence (522).

When the LOP has been determined controller 36 calculates a recommended tourniquet pressure (RTP) by adding a predetermined offset pressure level to the LOP. In the preferred embodiment the offsets added to the LOP to calculate an RTP are consistent with recommendations from the surgical literature and are calculated as follows: if the LOP is greater than 190 mmHg the RTP is calculated by adding 100 mmHg to the LOP; if the LOP is greater than 130 mmHg the RTP is calculated by adding 75 mmHg to the LOP; or if the LOP is less that 131 mmHg the RTP is calculated by adding 50 mmHg to the LOP. Controller 36 displays the measured LOP and the calculated RTP on display panel 28 and indicates that the measurement is complete. For example, if instrument 6 measures an LOP of 145 mmHg, then an RTP of 220 mmHg is calculated and both the LOP and RTP are shown on display panel 28. An operator may select the displayed RTP to be the reference pressure level or may manually select a different reference pressure level that is not based on LOP.

If during a LOP measurement controller 36 detects that the level of the non-pulsatile signal from non-pulsatile level detector 72 has exceeded a predetermined minimum or maximum limit level (522) controller 36 terminates the LOP measurement and opens deflation valve 54 to deflate cuff 10 (526). Examples of conditions that may cause the non-pulsatile signal to exceed the limits are the inadvertent removal of blood flow transducer 2 from the digit during the measurement, an excessive amount of venous blood accumulating in the digit, failure of the multi-conductor cable 8, or failure of transducer 2. Controller 36 also notifies the user by displaying an appropriate alarm message on display panel 28 and by audio tones produced by speaker 60.

Typical Use in Surgery

To enable a better understanding of the preferred embodiment, its typical use in a surgical procedure is described below.

An operator first selects an appropriately sized cuff 10 for application to patient limb 4 and secures cuff 10 around patient limb 4. Pneumatic passageways from instrument 6 to the inflatable portion of cuff 10 are completed by mating connectors 16 and 20, and connectors 18 and 22. Many different sizes and shapes of cuff 10 may be optionally used with instrument 6 to accommodate different physical sizes of patients and patient limbs. Cuffs may vary in length, width, shape, and application technique; also some cuffs may be applied with a soft limb protection sleeve located between the limb and the cuff. The specific level of pressure required in tourniquet cuff 10 to stop blood flow past cuff 10 at a particular time is affected by variables including the characteristics of cuff 10 and any underlying sleeve, the technique used in applying cuff 10, the physiological characteristics of the patient, and the physical characteristics of limb 4 at the location where cuff 10 is applied.

Accordingly, to assist in setting the reference pressure to the lowest and safest level, the operator of instrument 6 may choose to initiate a measurement of LOP. To perform a rapid and accurate measurement of LOP the operator first applies blood flow transducer 2 to a digit of patient limb 4 distal to the position of cuff 10. The operator then initiates the measurement of LOP by activating LOP key 34 on keypad 30. Instrument 6 then completes the LOP measurement within 20-40 seconds as described above, by automatically increasing the pressure in cuff 10 to a pressure at which arterial blood flow pulsations can no longer be detected by blood flow transducer 2. Instrument 6 then displays the resulting LOP on display panel 28, together with the RTP, and deflates cuff 10. Alternatively, to minimize time prior to surgery and to allow safe usage during surgery, if instrument 6 determines that an initiated LOP measurement is unlikely to be successfully completed due to any of a variety of factors then instrument 6 terminates the measurement shortly after the initiation, deflates cuff 10, displays a message on display panel 28 to alert the operator, and allows the operator to select a reference pressure level not based on LOP.

At the completion of the measurement of LOP, or upon termination of an initiated measurement, another measurement may be initiated or blood flow transducer 2 may be removed from patient limb 4 to allow other preparations for the surgical procedure to be completed.

The operator then selects a reference pressure level for the pressure of gas to be maintained in cuff 10 during the surgical procedure. The operator may choose to accept the displayed RTP as the reference pressure level or the operator may manually set another reference pressure level based on his or her judgment, experience or the institutional protocol. The subsequent inflation of cuff 10 to a pressure near the selected reference pressure level is then initiated by the operator depressing the "inflate" key on keypad 28. The pressure regulator of instrument 6 then operates to maintain the pressure of gas within cuff 10 near the selected reference pressure level. The reference pressure level may be adjusted and set to a new level at any time by the operator of instrument 6. At the completion of the surgical procedure, the operator initiates the deflation of cuff 10 by activating the deflate key on keypad 30. Cuff 10 is then removed from patient limb 4 immediately after deflation. Cuff 10 may be disconnected from instrument 6 by releasing connectors 16 and 20, and by releasing connectors 18 and 22.

We claim:

1. Tourniquet apparatus for rapidly and accurately measuring a patient's limb occlusion pressure comprising:
    an inflatable tourniquet cuff for encircling a limb at a location;
    a tourniquet instrument releasably connectable to the cuff and including
    pressure sensing means for producing a cuff pressure signal indicative of the level of pressure in the cuff,
    pressure regulation means communicating with the cuff and responsive to the cuff pressure signal for regulating the pressure in the cuff near a reference pressure level,
    blood flow transducing means adapted for applying to a portion of the limb distal to the cuff to transmit light through the portion of the limb, thereby to produce a blood flow signal indicative of blood flow in the portion,
    compensation means for compensating for reduction of the light transmission attributable to increases in the volume of venous blood in the portion of the limb; and limb occlusion pressure means responsive to the blood flow signal and the cuff pressure signal and operable for detecting arterial pulsations of blood flow, for increasing the reference pressure level in synchrony with the arterial pulsations and for producing a limb occlusion pressure value indicative of the lowest level of pressure in the cuff at which the magnitude of the arterial pulsations is less than a minimum detection threshold.

2. The tourniquet apparatus as defined in claim 1 wherein the limb occlusion pressure means further increases the reference pressure level in synchrony with a selected arterial pulsation from a first level to a second level that is equal to the sum of the cuff pressure level indicated by the cuff pressure signal at the time of the selected arterial pulsation plus an incremental pressure level.

3. The tourniquet apparatus as defined in claim 2 wherein the incremental pressure level is proportional to the difference between the magnitude of the selected arterial pulsation and a reference magnitude.

4. The tourniquet apparatus as defined in claim 1 wherein the limb occlusion pressure means is further operable during an initialization time period means for setting the reference pressure to an initial reference pressure level, and for producing an indication perceptible to an operator if the magnitude of arterial pulsations is not greater than a minimum initial magnitude during the initialization time period.

5. The tourniquet apparatus as defined in claim 4 wherein limb occlusion pressure means is further inoperable after the initialization time period if the indication is produced during the initialization time period and wherein the tourniquet instrument further includes means for enabling the reference pressure level to be set by an operator after the initialization time period if the indication is produced during the initialization time period.

6. The tourniquet apparatus as defined in claim 1 wherein the compensation means is further operable during a refractory time period, and during which period the limb occlusion pressure means is non-responsive to the blood flow signal for detecting arterial pulsations.

7. The tourniquet apparatus as defined in claim 6 wherein the compensation means is further operable during the refractory period of time for controlling the blood flow transducing means to increase the level of light transmitted through the portion of the limb.

8. Tourniquet apparatus for rapidly and accurately measuring a patient's limb occlusion pressure comprising:
a tourniquet cuff for encircling a patient's limb at a location on the limb and including an inflatable portion that communicates pneumatically with a first cuff port and that communicates pneumatically with a second cuff port independently of the first cuff port;
a tourniquet instrument that is releasably connectable to the first and second cuff ports to establish first and second pneumatic passageways between the tourniquet cuff and the tourniquet instrument, wherein the tourniquet instrument includes
pressure sensing means communicating with the first pneumatic passageway for producing a cuff pressure signal indicative of the level of pressure in the cuff,
pressure regulation means communicating with the second pneumatic passageway and responsive to the cuff pressure signal for regulating the pressure in the cuff near a reference pressure level,
blood flow signal processing means adapted for producing blood flow signals indicative of blood flow past the cuff and for processing the signals into non-pulsatile components as well as an arterial pulsations, and
limb occlusion pressure means for detecting the non-pulsatile components and the arterial pulsations for increasing the reference pressure level in synchrony with the arterial pulsations, and for producing a limb occlusion pressure value indicative of the lowest cuff pressure at which the magnitude of the arterial pulsations is less than a minimum detection threshold and for compensating for increases in the volume of venous blood in the patient's limb distal to the cuff that would, in the absence of compensation, reduce at least the level of the non-pulsatile component of the blood flow signal.

9. The tourniquet apparatus as defined in claim 8 wherein the limb occlusion pressure means is further operable during an initialization time period means for setting the reference pressure to an initial reference pressure level, and for producing an indication perceptible to an operator if the magnitude of arterial pulsations is not greater than a minimum initial magnitude during the initialization time period.

10. The tourniquet apparatus as defined in claim 9 wherein the limb occlusion pressure means further deflates the cuff and sets the reference pressure to zero if the indication is produced and wherein the tourniquet instrument further includes means for enabling an operator to manually increase the level of the reference pressure from zero after the indication is produced.

11. The tourniquet apparatus as defined in claim 8 wherein the limb occlusion pressure means is further non-responsive to the blood flow signal for a refractory period of time in synchrony with the arterial pulsations.

12. A method of rapidly and accurately measuring a patient's limb occlusion pressure comprising the steps of:
applying an inflatable tourniquet cuff to a patient's limb;
connecting the tourniquet cuff to a tourniquet instrument for inflating and the applied tourniquet cuff to a pressure near a reference pressure level;
measuring the pressure of gas within the inflated tourniquet cuff;
detecting, using light transmission, pulsations of arterial blood flow past the tourniquet cuff into the limb distal to the cuff;
compensating for reduction of the light transmission attributable to increases in the volume of venous blood in the patient's limb distal to the cuff;
increasing the reference pressure level in synchrony with the arterial pulsations; and
determining the lowest pressure of gas within the inflated tourniquet cuff at which the magnitude of the arterial pulsations is less than a minimum detection threshold.

13. The method of claim 12 wherein the compensating step is carried out during a refractory time period following the detecting step and during which time period the detecting step is suspended.

14. The method of claim 12 wherein the detecting step includes processing a blood flow signal to detect alternating variations in blood flow, thereby to determine the magnitudes of the arterial pulsations as the difference between a maximum and a minimum of a variation in blood flow.

* * * * *